United States Patent
Ookubo et al.

(10) Patent No.: US 6,966,891 B2
(45) Date of Patent: Nov. 22, 2005

(54) CATHETER

(75) Inventors: Itaru Ookubo, Fujinomiya (JP); Hiroyuki Yagami, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 72 days.

(21) Appl. No.: 10/647,512

(22) Filed: Aug. 26, 2003

(65) Prior Publication Data

US 2004/0106866 A1 Jun. 3, 2004

(30) Foreign Application Priority Data

Aug. 27, 2002 (JP) .............................. 2002-246986

(51) Int. Cl.⁷ .......................... A61M 31/00; A61B 8/12
(52) U.S. Cl. .......................... 604/103.04; 604/103.09; 600/467
(58) Field of Search .............................. 600/462–471; 604/103.04, 103.09, 164.13

(56) References Cited

U.S. PATENT DOCUMENTS

| | | | |
|---|---|---|---|
| 5,024,234 A * | 6/1991 | Leary et al. | 600/467 |
| 5,095,911 A * | 3/1992 | Pomeranz | 600/463 |
| 5,203,338 A | 4/1993 | Jang | |
| 5,400,789 A * | 3/1995 | Griffith | 600/466 |
| 5,405,318 A * | 4/1995 | Nita | 604/22 |
| 5,443,457 A * | 8/1995 | Ginn et al. | 604/528 |
| 5,501,227 A * | 3/1996 | Yock | 600/463 |
| 5,531,700 A * | 7/1996 | Moore et al. | 604/164.13 |
| 5,540,236 A * | 7/1996 | Ginn | 600/585 |
| 5,545,138 A * | 8/1996 | Fugoso et al. | 604/103.1 |
| 5,976,093 A * | 11/1999 | Jang | 600/462 |
| 6,022,319 A * | 2/2000 | Willard et al. | 600/470 |
| 6,312,406 B1 * | 11/2001 | Jayaraman | 604/102.01 |

* cited by examiner

*Primary Examiner*—Francis J. Jaworski
(74) *Attorney, Agent, or Firm*—Buchanan Ingersoll PC (57) ABSTRACT

A catheter includes a sheath main body portion, a first lumen, a sheath distal end portion, and a second lumen. The sheath main body portion is inserted into an organism. The first lumen is a passage provided in the sheath main body portion and through which a guide wire for guiding the sheath main body portion in an organism can be passed. The sheath distal end portion is provided on a lateral side of a distal end portion of the sheath main body portion. The second lumen is a passage different from the first lumen, provided in the sheath distal end portion, and through which a guide wire can be passed. The catheter can have both ease of exchange of catheter, which is the merit of an RX type catheter, and distal end pushing force transmission performance (pushability), which is the merit of an OTW type catheter.

16 Claims, 6 Drawing Sheets

A FORCE OF PUSHING THE CATHETER IS NOT TRANSMITTED TO THE DISTAL END OF THE CATHETER

THE BRANCHED LEFT UPPER SIDE

THE BRANCHED LEFT LOWER SIDE

CATHETER

BACKGROUND OF THE INVENTION

The present invention relates to a diagnostic catheter used for various kinds of diagnosis in the state of being inserted in a body cavity or lumen such as a blood vessel, a vas, and a digestive organ, and particularly to a rapid-exchange (RX) type catheter provided at its distal end with a lumen for insertion of a guide wire.

In a blood vessel insertion lumen represented by a catheter for use in Percutaneous Transluminal Coronary Angioplasty (PTCA) (this catheter will hereinafter be referred to as PTCA catheter), a guide wire lumen for insertion of a guide wire is provided over the whole length of the catheter in addition to a working lumen used for treatment or diagnosis.

The guide wire is inserted into the guide wire lumen prior to the insertion of the catheter into a blood vessel, and its distalcend precedes in the blood vessel to guide the distal end of the catheter to the vicinity of the diseased part (angiostenosis portion).

The catheter thus provided with the guide wire lumen over the whole length thereof is called an Over The Wire (OTW) type catheter.

For the PTCA procedure, a variety of catheters such as a dilation catheter, a stent delivery catheter, an atherectomy device, a rotoblator, a medicament injection catheter, an ultrasonic diagnostic catheter, etc. are used. In addition, the kind of catheter, the sizes of the balloon and stent of the dilation catheter, and the method of treatment are selected according to the properties of the angiostenosis portion and the conditions of the patient. Therefore, there are cases where exchange of the catheter is needed after the insertion into a blood vessel. Besides, in the case of setting a plurality of stents, also, the catheter may be drawn away and inserted a few times.

In the case of such an exchange of catheter, generally, it is preferable to keep the guide wire indwelling in the blood vessel, for the purposes of alleviation of burden on the patient, reductions in the operation time and labor, prevention of infection, etc.

In the conventional OTW type catheter, however, the guide wire lumen is provided over the whole length of the catheter as above-mentioned. Therefore, in order to exchange the catheter while keeping the guide wire indwelling in the blood vessel, the guide wire must project to the exterior at least beyond the whole length of the catheter. If the guide wire does not project to the exterior beyond the whole length of the catheter, the guide wire terminates at an intermediate position in the catheter, so that it is impossible to insert the catheter into an organism by operating the guide wire. Where the guide wire projects to the exterior beyond the whole length of the catheter, the guide wire projecting to the exterior is too long, resulting in that the operationality of the catheter is lowered by the guide wire.

As a countermeasure against this problem, there is the rapid-exchange (RX) type catheter provided with a guide wire lumen only at the distal end thereof. The RX type catheter includes a working lumen and a guide wire lumen. The working lumen is provided over the whole length of the catheter, and the guide wire lumen is provided substantially in parallel to the working lumen over a length of several centimeters at the distal end of the catheter. Thus, unlike the OTW type catheter, the RX type catheter is not provided with the guide wire lumen extending over the whole length of the catheter.

Therefore, in the RX type catheter, the guide wire lumen is shorter than that in the OTW type catheter, so that the guide wire need not be projecting to the exterior beyond the whole length of the catheter at the time of exchanging the catheter while keeping the guide wire indwelling in an organism. As a result, the catheter can be exchanged without spoiling the operationality of the catheter.

However, in the conventional RX type catheter, since the guide wire lumen is short, it is difficult for a force of pushing the catheter by the operator to be transmitted to the distal end of the catheter. In many cases, it is difficult for the distal end of the catheter to pass through an angiostenosis portion constituting the diseased part. In such an instance, it has been necessary to exchange the RX type catheter for an OTW type catheter so as to enable passage through the angiostenosis portion.

In addition, for enhancing the pushing force at the distal end of the catheter, it may be contemplated to enlarge the length of the guide wire lumen of the RX type catheter. In this case, however, as the length over which the working lumen and the guide wire lumen are parallel to each other is enlarged, the length of the portion of an increased outside diameter of the catheter is also enlarged accordingly. Thus, it is not preferable to enlarge the length of the guide wire lumen, in consideration of burden on the organism or the like.

SUMMARY OF THE INVENTION

The present invention has been made in consideration of the above-mentioned problems in the conventional catheters. Accordingly, it is an object of the present invention to provide a catheter having both the ease of exchange of catheter, which is the merit of an RX type catheter, and the distal end pushing force transmission performance (pushability), which is the merit of an OTW type catheter.

In order to attain the above object, according to one aspect of the present invention, there is provided a catheter including: a sheath main body portion to be inserted into an organism; a first lumen, which is a passage provided in the sheath main body portion and through which a guide wire for guiding the sheath main body portion in the organism can be passed; a sheath distal end portion provided on a lateral side of a distal end portion of the sheath main body; and a second lumen being a passage provided in the sheath distal end portion and different from the first lumen, the second lumen including a distal end opening portion and a proximal end opening portion through which a guide wire can be passed; wherein the first lumen is provided with an opening portion on the distal end portion in the direction of insertion into the organism so that the guide wire can be passed therethrough, and the proximal end opening portion of the second lumen is provided on the proximal end side in the insertion direction in relation to the opening portion of the first lumen within a distance of 60 mm from the opening portion of the first lumen.

Since the catheter is provided with the first lumen, which is provided in the sheath main body portion and through which the guide wire can be passed, and the second lumen, which is provided in the sheath distal end portion and through which the guide wire can be passed, the guide wire can be passed by selecting either one of the first lumen and the second lumen. In addition, it is also possible to pass the guide wire through both of the first lumen and the second lumen.

The catheter according to the present invention as described above may further be characterized as follows.

In the above catheter, the distal end opening portion of the second lumen may be provided at a distance of not less than 5 mm from the opening portion of the first lumen to the distal end side in the insertion direction.

According to this constitution, since the distal end opening portion of the second lumen is provided at a distance of not less than 5 mm from the opening portion of the first lumen to the distal end side in the insertion direction, the presence of both of the first lumen and the second lumen at the distal end of the catheter is obviated, so that the outside diameter of the catheter at the distal end can be reduced, thereby permitting smooth insertion of the catheter into an organism.

In the above catheter, the interval between the proximal end opening portion of the second lumen and the opening portion of the first lumen may be in the range of 2.5 to 10 mm.

According to this constitution, since the interval between the proximal end opening portion of the second lumen and the opening portion of the first lumen is set in the range of 2.5 to 10 mm, the strength of the catheter can be maintained to be high, without hampering the observation of the inside of an organism by use of the catheter.

In the above catheter, the opening portion of the first lumen may be opened into the passage of the second lumen.

According to this constitution, since the opening portion of the first lumen is opened into the passage of the second lumen, the guide wire passing through the first lumen is led into the second lumen at the distal end of the sheath main body portion and is projected from the second lumen into the organism. Therefore, a pushing force can be easily transmitted to the distal end of the sheath distal end portion.

In the above catheter, the opening portion of the first lumen is opened toward the inside of the organism.

According to this constitution, since the opening portion of the first lumen is opened toward the inside of the organism, by passing the guide wire through the first lumen and the second lumen it is possible to reinforce the catheter with the guide wire passed through the first lumen and the guide wire passed through the second lumen and to thereby easily guide the catheter to a diseased part.

In the above catheter, the sheath main body portion may have such a structure that an imaging core including an ultrasonic transducer at its distal end and capable of observing the inside of an organism can be passed through the sheath main body portion, in place of the first guide wire.

According to this constitution, since the imaging core can be passed through the sheath main body portion, in place of the first guide wire, it suffices to provide one passage for passage of the imaging core therethrough and for passage of the first guide wire therethrough, so that the catheter can be made smaller in diameter. In addition, the observation of the organism by the imaging core can be performed while using the same sheath main body portion having once been inserted into the organism, so that burden on the organism can be alleviated.

In the above catheter, the imaging core may be covered with a protective tube.

According to this constitution, since the imaging core is covered with the protective tube, the image core would not be damaged when being passed through the sheath main body portion in place of the first guide wire.

BRIEF DESCRIPTION OF THE DRAWINGS

The above and other objects, features, and advantages of the present invention become more apparent from the following detailed description in conjugation with the accompanying drawings, wherein.

DETAILED DESCRIPTION OF THE PREFERRED EMBODIMENTS

Now, embodiments of the present invention will be described referring to the drawings.

First Embodiment

Figure 1:
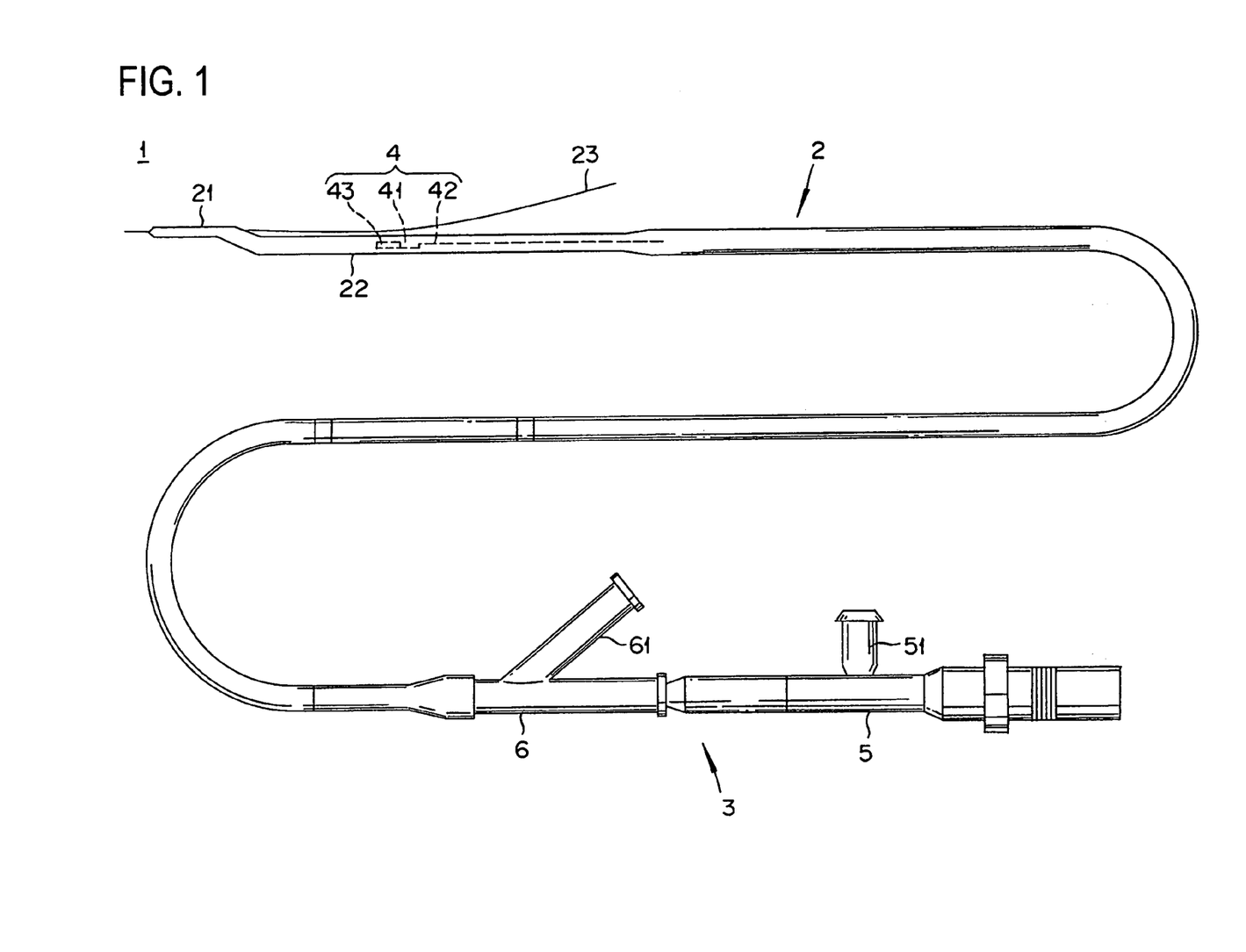
FIG. 1 illustrates an ultrasound catheter to which the present invention is applied.
Figure 2:
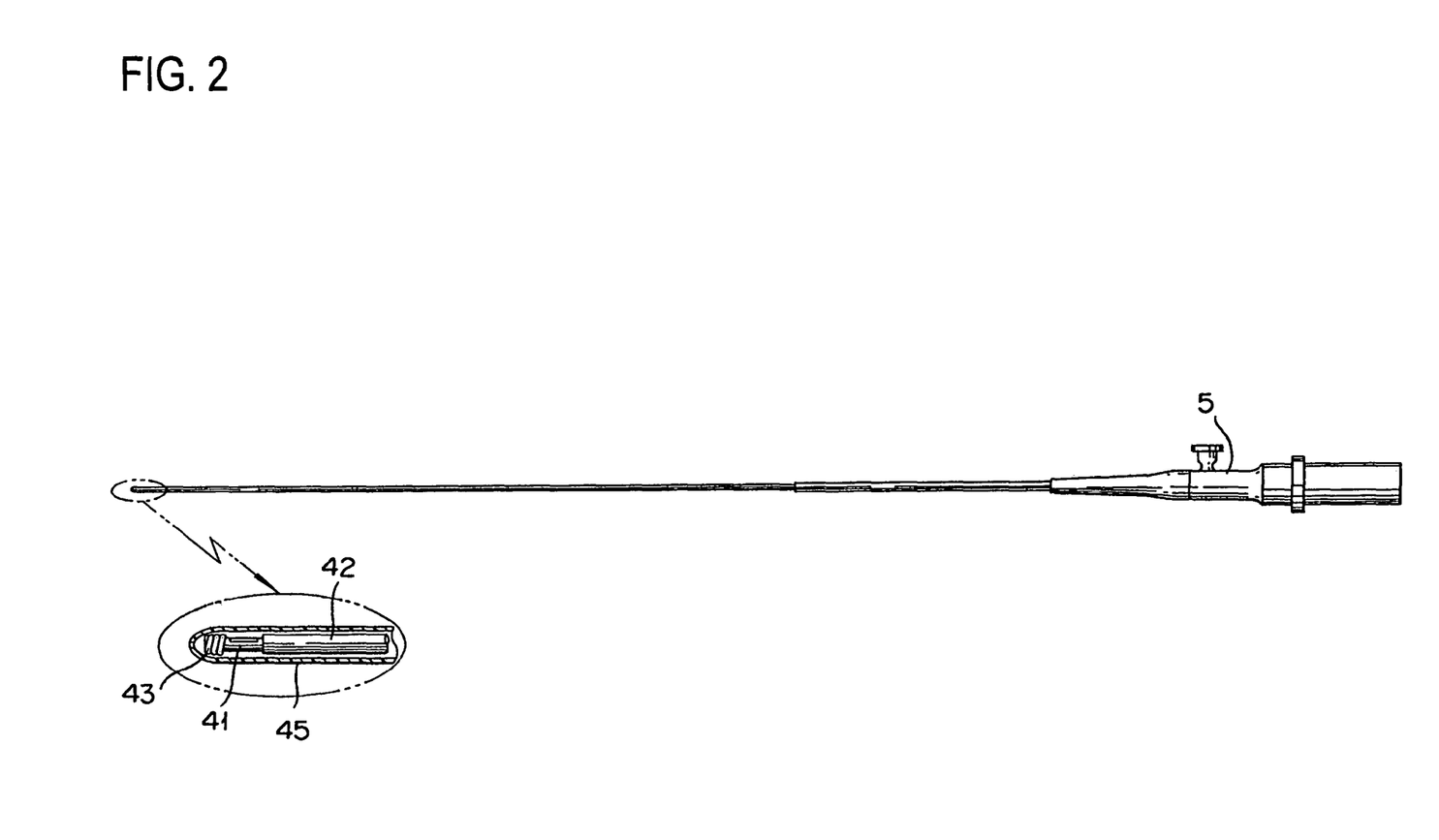
FIG. 2 illustrates an imaging core and a connector.

FIG. 1 illustrates an ultrasound catheter to which the present invention is applied, and FIG. 2 illustrates an imaging core and a connector.

The ultrasound catheter 1 shown in FIG. 1 is composed of a sheath 2 and an operating unit 3. The sheath 2 is inserted into a body cavity, and the operating unit 3 is not inserted into the body cavity but is disposed on the side of the hand or fingers of the user for operation by the user.

The sheath 2 includes a sheath distal end portion 21 and a sheath main body portion 22. The sheath distal end portion 21 is provided on a lateral side of a distal end portion of the sheath main body portion 22 so as to have an axis different and deflected from the center axis of the sheath main body portion 22. The sheath distal end portion 21 is provided with a straight lumen (second guide wire lumen) through which a guide wire 23 can be passed, in the same manner as a conventional RX type catheter.

In addition, the sheath main body portion 22 is also provided therein with a lumen over the whole length thereof, and the guide wire 23 or an imaging core 4 is passed through the lumen. The lumens provided in the sheath distal end portion 21 and the sheath main body portion 22 are substantially parallel to each other, and the lumen provided in the sheath distal end portion 21 is much shorter than the lumen provided in the sheath main body portion 22. Besides, the overlap distance where the sheath distal end portion 21 and the sheath main body portion 22 are both present is set to be extremely short. In FIG. 1, description will be made assuming that the imaging core 4 is passed through the sheath main body portion 22. FIG. 2 shows the condition where the imaging core 4 has been drawn out of the sheath main body portion 22.

The imaging core 4 is composed of an ultrasonic transducer 41, a drive shaft 42, and a rotation stabilizing coil 43. The imaging core 4 is connected to a connector 5 as shown in FIG. 2. After the sheath 2 is inserted into an organism, the ultrasonic transducer 41 generates an ultrasound toward the inside of the organism and receives the ultrasound returning after being reflected, whereby it is possible to form an ultrasonic tomographic image of a diseased part.

The drive shaft 42 is flexible and has such a characteristic property that a rotational force generated at the operating unit 3 can be transmitted therethrough to the ultra sonic transducer 41. The drive shaft 42 is composed, for example, of a tubular member in the form of a multilayer coil such as a trilayer coil in which the winding direction is alternately changed in the manner of right-left-right. With the rotational force transmitted by the drive shaft 42, the ultrasonic transducer 41 is rotated, whereby the diseased part in a body cavity such as a blood vessel and a vas can be observed in a 360-degree mode. In addition, a signal cable for transmitting a signal detected by the ultrasonic transducer 41 to the operating unit 3 is extended inside the drive shaft 42.

The rotation stabilizing coil 43 is attached to the distal end of the ultrasonic transducer 41 and functions as a guide for stable rotation of the ultrasonic transducer 41 when the imaging core 4 is rotated.

Besides, as shown in an enlarged part in FIG. 2, the imaging core 4 is covered with a protective tube 45. The protective tube 45 is fixed to the connector 5, which will be described later, is not rotated together with the drive shaft 42, and secures safety at the distal end portion. The protective tube 45 is provided with an opening at the distal end thereof.

The operating unit 3 includes the connector 5 and a hub 6. The connector 5 is connected to the distal end of the imaging core 4 and includes a protective tube, which is not shown, and a port 51 for supplying an ultrasound transfer liquid into the sheath 2. The hub 6, also, includes a similar port 61.

The ultrasound transfer liquid supplied via the port 51 and the port 61 flows through the protective tube and the sheath main body portion 22 to fill up the range from the proximal end side to the distal end side of the sheath 2, namely, flows to fill up the portion ranging from the proximal end side to the distal end side in the direction of insertion of the sheath 2 into an organism. Incidentally, the opening provided at the distal end of the protective tube 45 ensures that the ultrasound transfer liquid is charged and circulated also in the protective tube 45. Then, the opening permits transmission of the ultrasound generated by the ultrasonic transducer 41.

After the sheath 2 is filled up with the ultrasound transfer liquid, the sheath 2 is inserted into a body cavity or the like, whereby the ultrasound transfer liquid is disposed between the ultrasonic transducer 41 and the blood vessel wall. Then, the ultrasound can be transmitted through the ultrasound transfer liquid to a diseased part, is reflected by the diseased part, and returns from the diseased part. Owing to the presence of the ultrasound transfer liquid, the ultra sonic transducer 41 can pick up an ultra sonic video signal. As the ultrasound transfer liquid, a physiological saline or the like is used. The physiological saline enables the ultrasonic transducer 41 to transmit and receive an ultrasound and is inert to the human body when being discharged from the distal end of the sheath 2 into the body.

The connector 5 holds the drive shaft 42 of the imaging core 4, and is connected to a motor not shown, so as to transmit a rotational force of the motor to the ultrasonic transducer 41 through the drive shaft 42.

The hub 6 is connected to the proximal end of the sheath main body portion 22 and is independent from the connector 5. The hub 6 is provided also with the port 61, in addition to a first distal end opening portion into which the imaging core 4 is inserted as shown in FIG. 1. The port 61 of the hub 6 can be used also for injection of a medicament. The medicament supplied through the port 61 is fed from the proximal end side toward the distal end side of the sheath 2 through the inside of the sheath main body portion 22, in the same manner as the ultrasound transfer liquid. A side hole is provided in the vicinity of the distal end of the sheath main body portion 22, and the medicament is discharged through the side hole into the body. Thus, by injecting the medicament, the ultrasound catheter 1 can be used also as a medicament injection catheter. Incidentally, the hub 6 may have a structure such that a known Y type connector can be selectively attached to the distal end of the sheath 2.

Next, referring to FIG. 3, the structures on the distal end side of the sheath distal end portion 21 and the sheath main body portion 22, which constitute a characteristic feature of the present invention, will be described.

Figure 3:
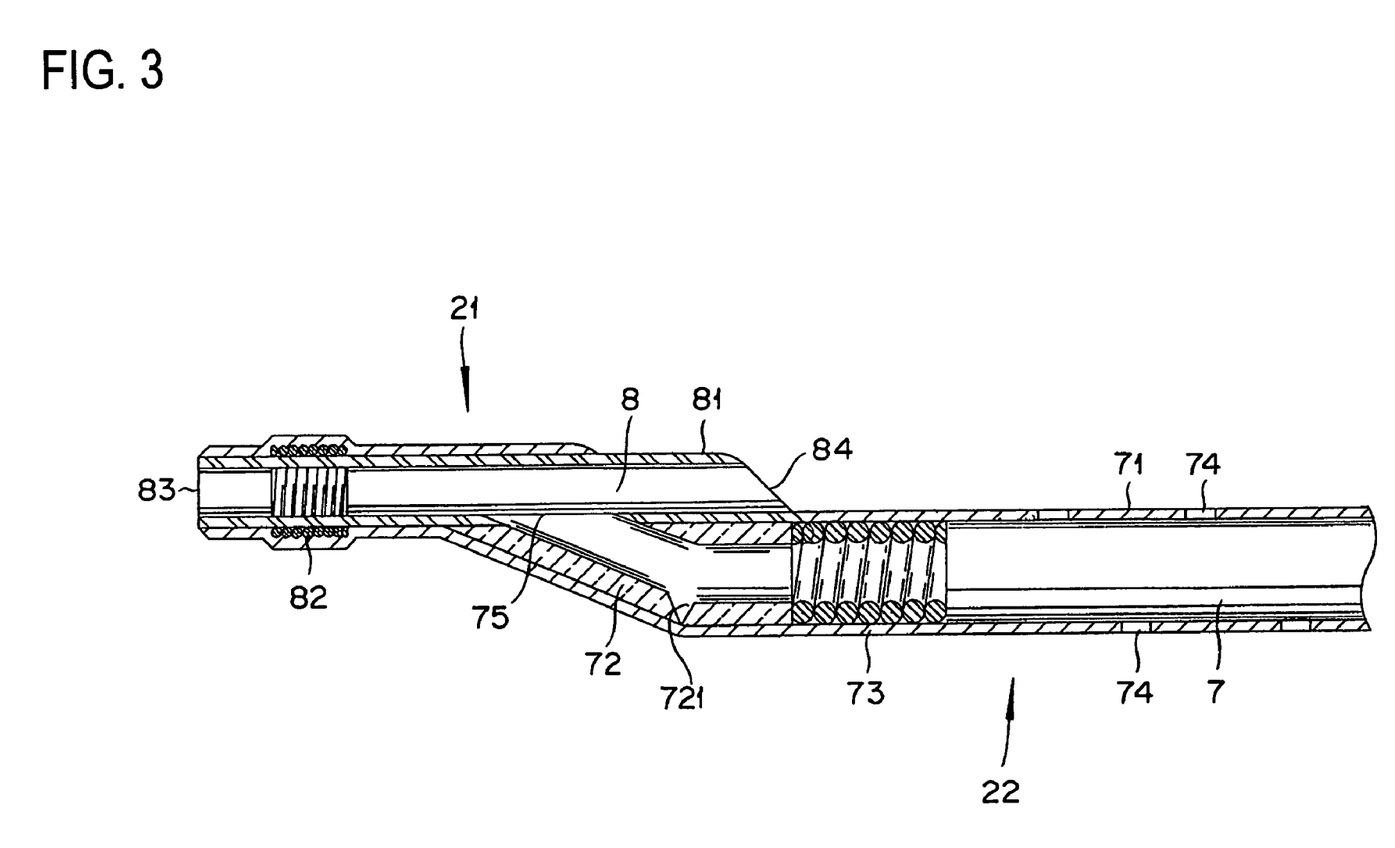
FIG. 3 is a sectional view showing the constitution of the neighborhood of the distal end of a sheath.

FIG. 3 is a sectional view showing the constitution of the neighborhood of the distal end of the sheath 2.

As shown in FIG. 3, the sheath main body portion 22 extends from the side of the distal end of the sheath 2, is composed of a catheter tube 71 and a reinforcing part 72, and is provided therein with a first lumen 7.

As has been mentioned above, the first lumen 7 is a lumen through which the imaging core 4 can be passed. The first lumen 7 further plays the role of a guide wire lumen through which the guide wire 23 can be passed, in place of the imaging core 4. Here, the guide wire to be passed through the first lumen 7 is similar to the above-mentioned guide wire 23.

A kink preventive coil 73 is provided at the distal end of the first lumen 7, namely, at the distal end in the direction of insertion into an organism of the catheter tube 71. The kink preventive coil 73 functions to reinforce the joint portion between the sheath main body portion 22 and the sheath distal end portion 21 for preventing the sheath 2 from kinking. In addition, the catheter tube 71 is provided with a plurality of side holes 74 in spiral shape, through which a medicament or the like can be discharged into an organism.

The reinforcing part 72 is attached to the distal end of the catheter tube 71. The reinforcing part 72 is formed of a resin and changes the direction of the first lumen 7 extending from the catheter tube 71 toward a second lumen 8, which will be described later, of the sheath distal end portion 21 so as to join the first lumen 7 to the second lumen 8.

In addition, the reinforcing part 72 further reinforces the joint portion between the sheath main body portion 22 and the sheath distal end portion 21 to prevent kinking. Here, the reinforcing part 72 is provided with a bend assisting slit 721, which ensures that at the time of passing the guide wire 23 through the portion ranging from the first lumen 7 to a second distal end opening portion 83 and inserting the sheath 2 into an organism, the portion ranging from the sheath 2 to the second distal end opening portion 83 can be easily deformed into a rectilinear form. As a result, a burden on the sheath 2 can be absorbed to prevent the sheath 2 from being kinked by the burden. The reinforcing part 72 includes a first distal end opening portion 75 opened toward the inside of the second lumen 8.

The sheath distal end portion 21 is attached to a lateral side of the reinforcing part 72, namely, on a lateral side of the distal end portion of the sheath main body portion 22. The sheath distal end portion 21 is composed of a distal end tube 81 and an X-ray contrast coil 82. The distal end tube 81 is provided with a second lumen 8, as a guide wire lumen through which a guide wire (second guide wire) can be passed.

The second lumen 8 is communicated with the first distal end opening portion 75 of the first lumen 7 of the sheath main body portion 22. The second lumen 8 is provided with a second distal end opening portion 83 opened at a distance of not less than 5 mm to the distal end side from the opening portion 75. The second lumen 8 is also provided with a proximal end opening portion 84 opened within a distance of 60 mm to the proximal end side from the opening portion 75. Therefore, the guide wire 23 can pass through the distal end opening portion 83 to the proximal end opening portion 84. Since the distal end opening portion 83 of the second lumen 8 is opened at a distance of not less than 5 mm to the distal end side from the first distal end portion 75 of the first lumen 7, the presence of both the first lumen 7 and the second lumen 8 at the distal end portion of the ultrasound catheter 1 is obviated, making it possible to reduce the outside diameter of the ultrasound catheter 1 at the distal end portion thereof and to smoothly insert the ultrasound catheter 1 into an organism.

The above-mentioned numerical values are preferable, for the following grounds.

(i) In order to guide the ultrasound catheter 1 along the guide wire 23, it is necessary for the length of the second lumen 8 to be not less than a certain value. Specifically, the length is preferably not less than 10 mm.

(ii) It is not preferable that the distal end opening portion 83 and the ultrasonic transducer 41 are much spaced from each other. Specifically, the spacing is preferably within 100 mm.

(iii) The interval between the second proximal end opening portion 84 of the second lumen 8 and the distal end opening portion 75 of the first lumen 7 is, in other words, the overlapping (coexistence) portion of the sheath main body portion 2 and the distal end tube 81, so that the outside diameter of the ultrasound catheter 1 is increased over the range of the overlapping (coexistence) portion, and the position of the ultrasonic transducer 41 must be moved to the proximal end side. Although it is possible to set the position of the ultrasonic transducer 41 at a position where the distal end tube 81 is present, the distal end tube 81 can hamper the pickup of a video image. Therefore, it is not preferable that the two members overlap with each other. Therefore, it is preferable that the overlapping portion of the sheath main body portion 2 and the distal end tube 81 is set to be short. Accordingly, the length of the overlapping portion of both the members is preferably in the range of 0 to 60 mm, a more preferable range is 2 to 10 mm, and a further preferable range is 3 to 5 mm.

In the above embodiment, the proximal end opening portion 84 is inclined from the axial direction of the ultrasound catheter 1 toward the distal end by about 20 to 70 degrees, whereby the overlapping portion of the sheath main body portion 2 and the distal end tube 81 is reduced while making the same the range of joint between the sheath main body portion 2 and the distal end tube 81; this also solves the problem as to strength and outside diameter.

The X-ray contrast coil 82 is wound around the vicinity of the distal end portion of the distal end tube 81, so as to ensure that the position of the sheath distal end portion 21 is visible under fluoroscopy when the ultrasound catheter 1 is inserted into a body cavity.

The sheath distal end portion 21 and the sheath main body portion 22 are so disposed that the sheath distal end portion 21 is enveloped with the catheter tube 71 of the sheath main body portion 22, and they are firmly fixed by use of an adhesive, heat seal or the like.

As has been described above, in the ultrasound catheter 1 according to the present invention, the first lumen 7 is joined to an intermediate portion of the second lumen 8. Therefore, the guide wire 23 passed through the first lumen 7 can pass via the first distal end opening portion 75 into the second lumen 8 and pass via the second distal end opening portion 83 to the exterior of the sheath 2. In this case, the guide wire 23 is passed over the whole length of the sheath main body portion 22. Therefore, the ultrasound catheter 1 can play the role of a conventional OTW type catheter.

In addition, since the second lumen 8 is provided in a rectilinear form, when the guide wire 23 is passed through the second distal end opening portion 83 of the second lumen 8 and through the second proximal end opening portion 84, the ultrasound catheter 1 can play the role of a conventional RX type catheter.

Next, a specific example of utilization of the ultrasound catheter 1, which can play the roles of both the OTW type catheter and the RX type catheter, will be shown.

FIGS. 4A to 4F are general views showing an example of utilization of the ultrasound catheter. In FIGS. 4A to 4F, for ease of recognizing the guide wire 23, the portion of the guide wire 23 passing through the sheath is shown in a void form, and the other portions are shown in a solid form.

Figure 4A:
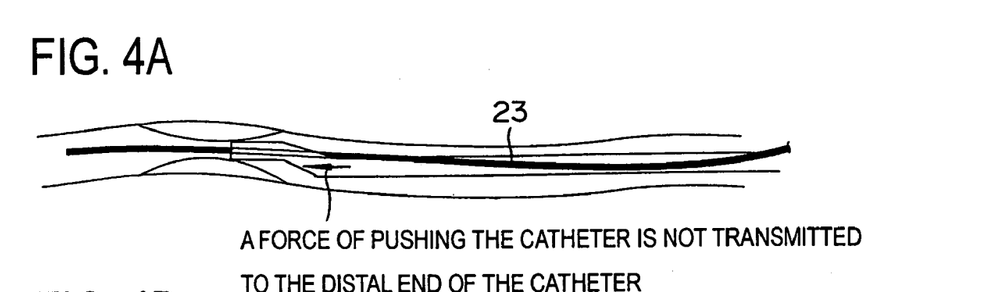
FIGS. 4A to 4F are general views for illustrating an example of utilization of the ultrasound catheter.

First, as shown in FIG. 4A, the ultrasound catheter 1 according to the present invention is used as an RX type catheter, i.e., the guide wire 23 is passed through the second lumen 8, and the ultrasound catheter 1 is inserted into an organism under the guiding by the guide wire 23. The ultrasound catheter 1 is first used as the RX type catheter, because the use as the RX type permits more swift exchange of the catheter than in the case of the use as the OTW type and permits the imaging core 4 to be preliminarily inserted, so that burden on an organism is light if it suffices to use the catheter as the RX type only.

In the case of using the catheter as an RX type catheter, however, the guide wire 23 is passed only through the sheath distal end portion 21, so that the sheath distal end portion 21 becomes more difficult to bend than the sheath main body portion 22. This results in that, as indicated by an arrow in FIG. 4A, the pushing force for pushing the ultrasound catheter 1 into a lumen is not transmitted to the sheath distal end portion 21 but transmitted only to the distal end of the sheath main body portion 22. Therefore, in the case where a stenosis portion is present in the lumen, the pushing force may be too small to advance the catheter beyond the stenosis portion.

Figure 4B:
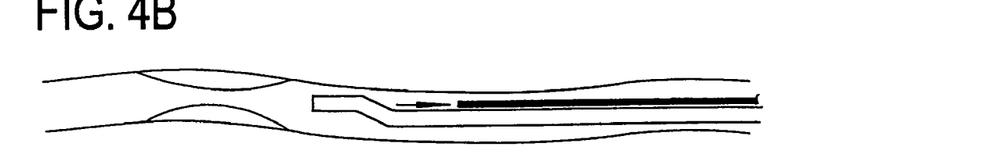

In such an instance, as shown in FIG. 4B, only the guide wire 23 is drawn out of the organism, with the ultrasound catheter 1 itself indwelling in the organism.

Figure 4C:
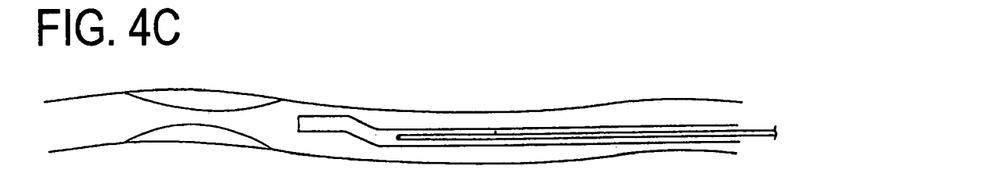

Then, as shown in FIG. 4C, the ultrasound catheter 1 is used as an OTW type catheter, and the guide wire 23 is passed through the sheath main body portion 22 over the whole length of the sheath main body portion 22. Here, the guide wire 23 cannot be passed through the sheath main body portion 22 if the imaging core 4 is inserted in the sheath main body portion 22. Therefore, the imaging core 4 is drawn out of the sheath main body portion 22 by gripping the connector 5, and then the guide wire 23 is inserted from the hub 6.

Figure 4D:
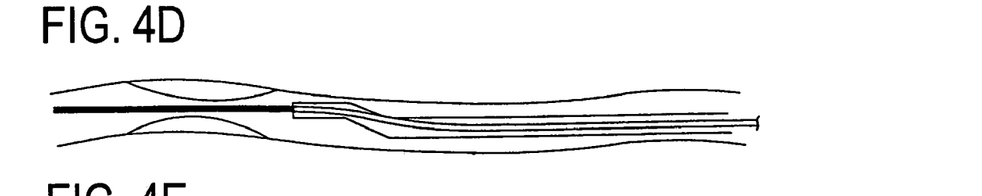

The guide wire 23 inserted from the hub 6 is passed through the sheath main body portion 22 and the sheath distal end portion 21 into the lumen, as shown in FIG. 4D. The guide wire 23 thus passed into the lumen is operated on the proximal end side of the ultrasound catheter 1 and is advanced beyond a stenosis portion in the lumen prior to the ultrasound catheter 1.

Figure 4E:
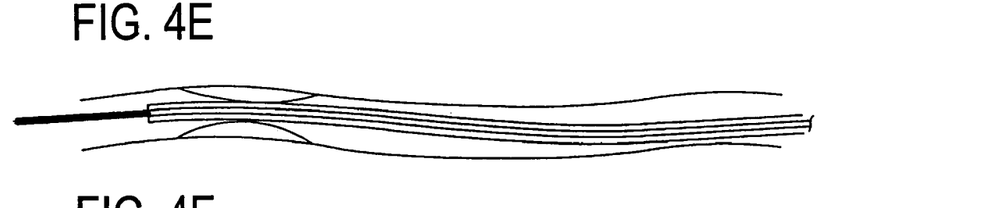

Next, as shown in FIG. 4E, the ultrasound catheter 1 is pushed in along the guide wire 23 to pass through the stenosis portion. Here, since the ultrasound catheter 1 is used as the OTW type catheter, the pushing force can be transmitted also to the sheath distal end portion 21, so that the passage through the stenosis portion can be easily achieved.

Figure 4F:
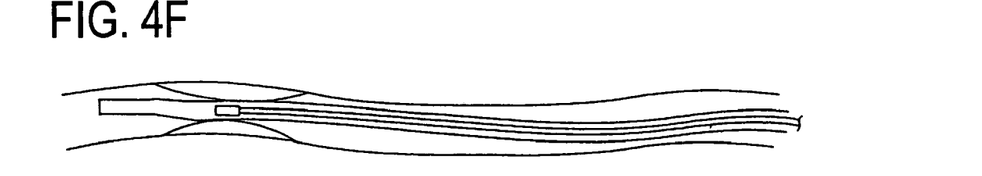

Then, while the ultrasound catheter 1 passed through the stenosis portion is left indwelling, the guide wire 23 is drawn out of the sheath distal end portion 21 and the sheath main body portion 22. Alternatively, the imaging core 4 attached to the connector 5 is inserted into the sheath main body portion 22, as shown in FIG. 4F. The imaging core 4 thus inserted is positionally adjusted to the stenosis portion constituting the diseased part by operating the connector 5, to be used for diagnosis of the diseased part.

Thus, since in the present invention the second lumen 8 extending in the sheath distal end portion 21 and the first lumen 7 extending in the sheath main body 22 are provided as lumen for the guide wire 23, the lumen through which to pass the guide wire 23 can be selected according to the circumstances. By appropriately changing the lumen through which to pass the guide wire 23, it is possible to easily insert the ultrasound catheter 1 into an organism while reducing the burden on the organism.

In addition, since in the ultrasound catheter 1 the length of the sheath distal end portion 21 is set to be smaller than that of the sheath main body portion 22, the length over which the sheath distal end portion 21 and the sheath main body portion 22 are present in parallel to each other is small, so that the range of the larger diameter portion of the ultrasound catheter 1 inserted into an organism is limited, thereby reducing the burden on the organism.

Furthermore, since the opening portion 75 of the first lumen 7 is opened toward the second lumen 8, the guide wire 23 passed through the first lumen 7 is led into the second lumen 8 at the distal end of the sheath main body portion 22 and is projected via the second lumen 8 into an organism. Therefore, the pushing force can be easily transmitted to the distal end of the sheath distal end portion 21.

In addition, since the imaging core 4 can be passed through the sheath main body portion 22 in place of the guide wire 23, the sole lumen can function as both a lumen for passing the imaging core 4 therethrough and a lumen for passing the guide wire 23 therethrough, making it possible to reduce the diameter of the portion of the ultrasound catheter 1 inserted into an organism. Besides, since the organism can be observed through the imaging core 4 by use of the same sheath main body portion 22 as that once inserted into the organism, the burden on the organism can be alleviated.

Moreover, since the imaging core 4 is covered with the protective tube 45, the imaging core 4 would not be damaged at the time of passing the imaging core 4 in the sheath main body portion 22 or drawing out the imaging core 4, as has been described above. In addition, since the imaging core 4 is protected by the protective tube 45, even when the drive shaft 42 is rotated at a high speed, the imaging core 4 would not be broken, and the inside of the sheath main body portion 22 would also not be broken. Further, since the presence of the protective tube 45 prevents the imaging core 4 from making direct contact with an organism even where the imaging core 4 is passed through the sheath main body portion 22 into the organism, the organism would not be injured due to high-speed rotation of the drive shaft 42.

Second Embodiment

Next, a case where the above-described ultrasound catheter 1 is partly improved will be described. The ultrasound catheter 1 in this second embodiment is different from the first embodiment in that the first lumen 7 provided in the sheath main body portion 22 is not communicated with the second lumen 8 provided in the sheath distal end portion 21 but opened to the exterior of the sheath main body portion 22, namely, toward an organism.

Figure 5:
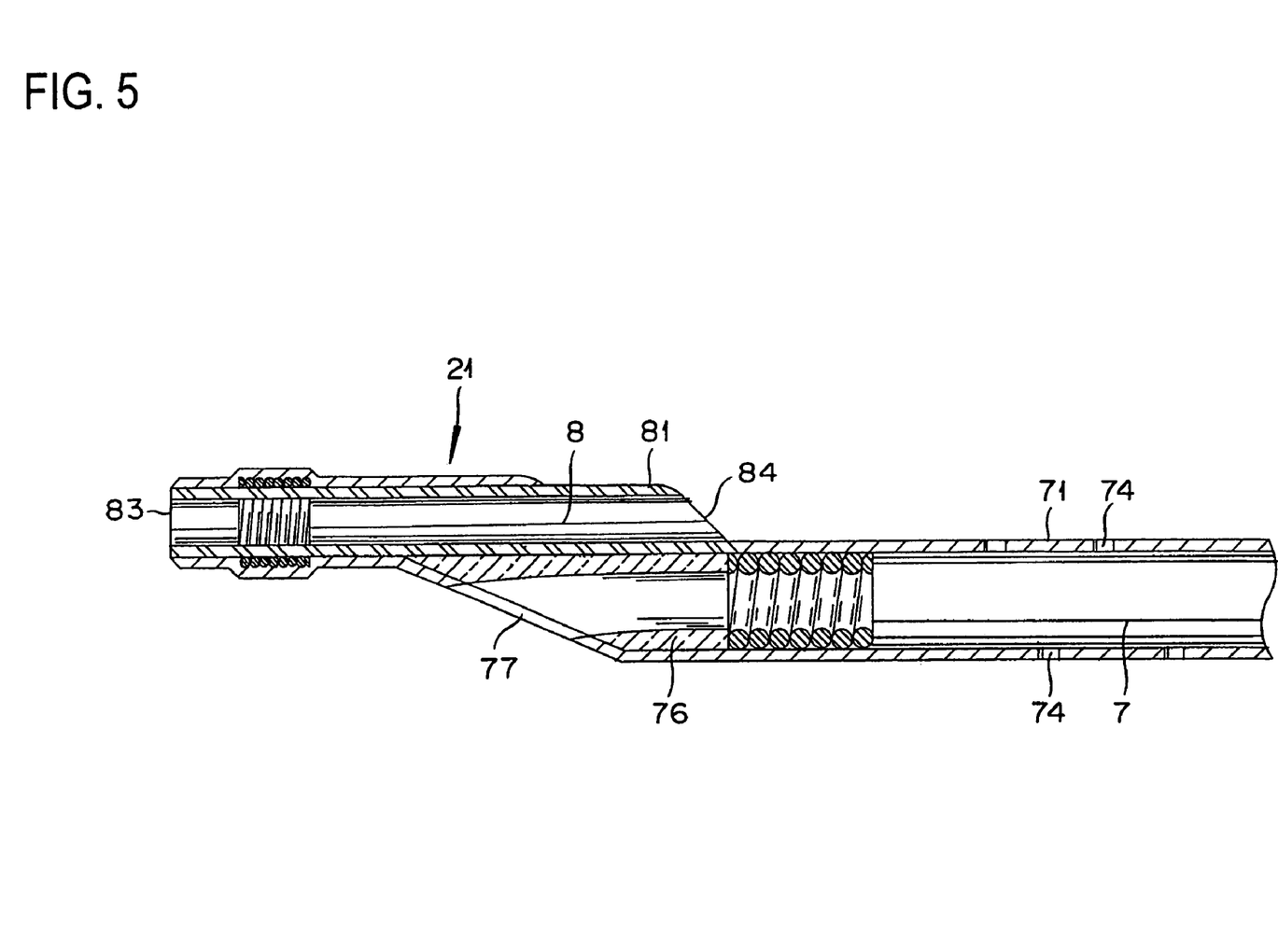
FIG. 5 is a sectional view showing the constitution of a sheath distal end portion and a sheath main body portion in a second embodiment.

FIG. 5 is a sectional view showing the constitution of the sheath distal end portion and the sheath main body portion according to the second embodiment. Since the ultrasound catheter 1 in the second embodiment is nearly the same with the ultrasound catheter 1 in the first embodiment, the same components as those in the first embodiment are denoted by the same reference numerals as used above, and description thereof is omitted.

In the second embodiment, a reinforcing part 76 is attached to the catheter tube 71. The reinforcing part 76 is formed of a resin and includes a first distal end opening portion 77 so that the first lumen 7 extending through the catheter tube 71 is opened toward the inside of an organism. Therefore, unlike in the first embodiment, the first lumen 7 is not joined to the second lumen 8. The guide wire 23 passed in the sheath main body portion 22 is passed directly through the sheath main body portion 22 to project into the organism. Here, the first distal end opening portion 77 is preferably provided in the state of being slightly inclined to the direction of parting away from the second lumen 8.

Thus, in the second embodiment, unlike in the first embodiment, the first lumen 7 and the second lumen 8 are not communicated with each other but independent from each other.

Figure 6:
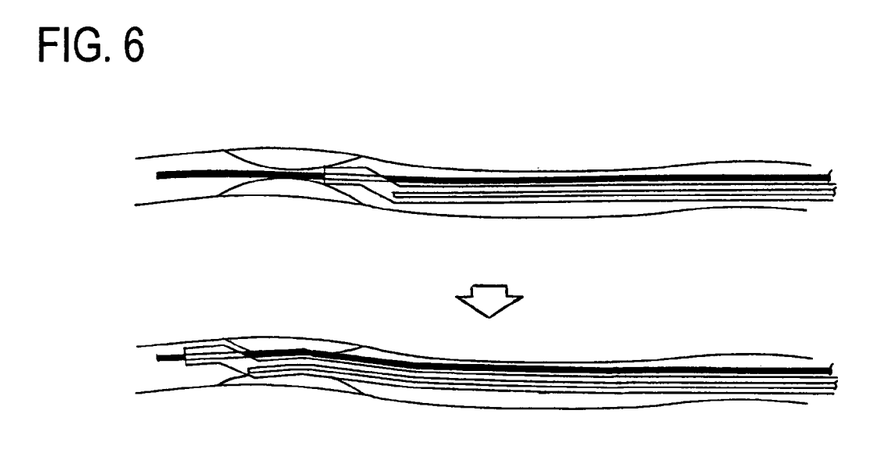
FIG. 6 illustrates an example of utilization of the ultrasound catheter in the second embodiment.
Figure 7:
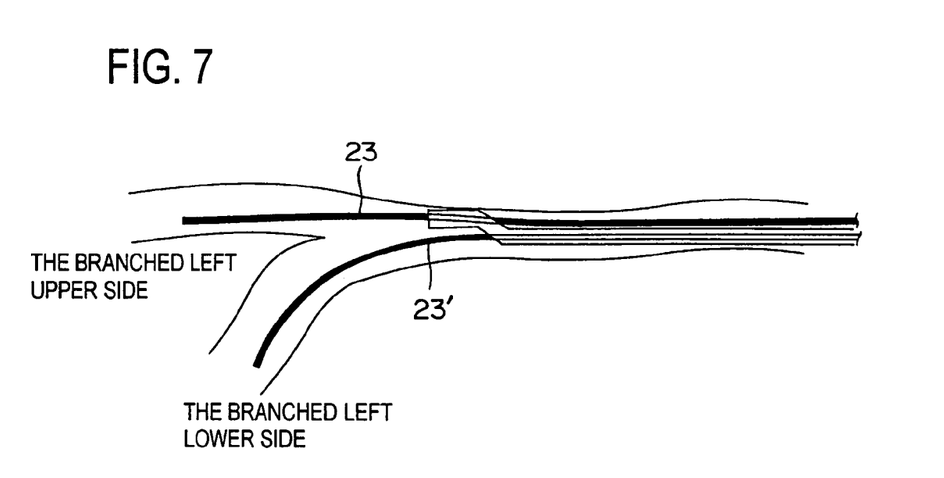
FIG. 7 illustrates an example of utilization of the ultrasound catheter in the second embodiment.

FIGS. 6 and 7 illustrate an example of utilization of the ultrasound catheter 1 in the second embodiment.

As shown in FIG. 6, passing guide wires 23 respectively through the first lumen 7 and the second lumen 8 can reinforce the whole body of the sheath 2. Therefore, the ultrasound catheter 1 can be easily passed through a stenosis portion by the two guide wires 23, even in the case where the use of the ultrasound catheter 1 as an RX type catheter makes it difficult to pass the ultrasound catheter 1 through the stenosis portion.

Further, for example where a plurality of portions are to be treated, as shown in FIG. 7, after the treatment of a first portion, the second guide wire 23' can be guided to a branch point for branching to the other portion to be treated. More specifically, for the treatment (diagnosis) of the branched left upper side in FIG. 7, the ultrasound catheter 1 is guided by use of the guide wire 23, and after the treatment (diagnosis) is finished, the other guide wire 23' can be guided to the branch point for branching to the portion to be treated next (the branched left lower side) by use of he first lumen 7 of the ultrasound catheter 1. This makes it possible to easily guide the guide wire 23' to the branch point without fear of damaging the organism. At the branch point, the inclination of the first distal end opening portion 77 makes it easy to guide the guide wire 23' toward the branching direction.

Thus, in the second embodiment, since the first distal end opening portion 77 of the first lumen 7 is opened toward the inside of an organism, by passing the guide wires 23 and 23' respectively through the first lumen 7 and the second lumen 8, it is possible to reinforce the sheath 2 of the ultrasound catheter 1 and to easily pass the ultrasound catheter 1 through a stenosis portion by the guide wire 23 passed through the first lumen 7 and the guide wire 23, passed through the second lumen 8. In addition, where there are a plurality of portions to be treated, it is easy to insert the guide wire to the portion to be treated next.

Besides, in the second embodiment, the second proximal end opening portion 84 of the second lumen 8 may be located on the distal end side in the insertion direction in relation to the first distal end opening portion 77.

While description has been made taking the ultrasound catheter 1 as an example in the first and second embodiment above, the present invention is applicable not only to the ultrasound catheter 1 but also to other various catheters such as a dilation catheter, a stent delivery catheter, an atherectomy device, and a medicament injection catheter.

While preferred embodiments of the invention have been described using specific terms, such description is for illustrative purposes only, and it is to be understood that changes and variations may be made without departing from the spirit or scope of the following claims.

What is claimed is:

1. A catheter comprising:
    a sheath main body portion to be inserted into an organism;
    a first lumen, which is a passage provided in said sheath main body portion, which has a first axis, and through which a guide wire for guiding said sheath main body portion in said organism can be passed, said first lumen comprising a first distal end opening portion, which is provided on the distal end side in the direction of insertion into said organism and through which said guide wire can be passed, and a first proximal end opening portion, which is provided on the proximal end side and through which said guide wire can be passed;
    a sheath distal end portion provided at a distal end portion of said sheath main body portion; and
    a second lumen being a passage different from said first lumen, said second lumen being provided in said sheath distal end portion, said second lumen comprising a second distal end opening portion and a second proximal end opening portion through which a guide wire can be passed, and said second lumen having a second axis different from said first axis;
    said sheath main body portion comprising a reinforcing part at a joint portion between said sheath main body portion and said sheath distal end portion, a portion of said first lumen extending through said reinforcing part; wherein
    said second proximal end opening portion of said second lumen is provided on the distal end side of a position at a distance of 60 mm from said first distal end opening portion of said first lumen toward the proximal end side along said insertion direction.

2. The catheter as set forth in claim 1, wherein said second proximal end opening portion of said second lumen is provided on the distal end side of a position at a distance of 5 mm from said first distal end opening portion of said first lumen toward the proximal end side along said insertion direction.

3. The catheter as set forth in claim 1, wherein the spacing between said second proximal end opening portion of said second lumen and said first distal end opening portion of said first lumen is in the range of 2.5 to 10 mm.

4. The catheter as set forth in claim 1, wherein said first distal end opening portion of said first lumen is opened into the passage of said second lumen.

5. The catheter as set forth in claim 1, wherein said first distal end opening portion of said first lumen is opened to the exterior of the passage of said second lumen.

6. The catheter as set forth in claim 1, wherein an imaging core provided with an ultrasonic transducer at the distal end of said imaging core and enabling observation of the inside of said organism can be passed through said first lumen, in place of said guide wire.

7. The catheter as set forth in claim 6, wherein said imaging core is covered with a protective tube.

8. The catheter as set forth in claim 1, wherein said sheath distal end portion has a distal end which extends distally beyond a distal end of said sheath main body portion.

9. The catheter as set forth in claim 8, wherein an axial length of said sheath distal end portion is less than an axial length of said sheath main body portion.

10. The catheter as set forth in claim 1, wherein said second distal end opening portion is positioned distally of said first distal end opening portion.

11. The catheter as set forth in claim 10, wherein an axial length of said sheath distal end portion is less than an axial length of said sheath main body portion.

12. The catheter as set forth in claim 1, wherein said sheath main body portion comprises a catheter tube, and said reinforcing part is located in said catheter tube.

13. The catheter as set forth in claim 12, wherein said reinforcing part is located only at the joint portion between said sheath main body portion and said sheath distal end portion.

14. The catheter as set forth in claim 12 further comprising a coil located proximally of the reinforcing part.

15. The catheter as set forth in claim 1, wherein said reinforcing part is located only at the joint portion between said sheath main body portion and said sheath distal end portion.

16. The catheter as set forth in claim 1, further comprising a coil located proximally of the reinforcing part.

* * * * *